United States Patent [19]
Vandewalle

[11] Patent Number: 5,782,922
[45] Date of Patent: Jul. 21, 1998

[54] METHOD AND APPARATUS FOR REPLACING THE CAPITELLUM

[75] Inventor: Mark Victor Vandewalle, Pierceton, Ind.

[73] Assignee: Biomet, Inc., Warsaw, Ind.

[21] Appl. No.: 797,291

[22] Filed: Feb. 7, 1997

[51] Int. Cl.$^6$ .............................. A61F 2/38; A61F 5/00
[52] U.S. Cl. .......................................... 623/20; 606/87
[58] Field of Search ...................... 623/18, 20; 606/80, 606/82, 84, 87, 88, 89, 96

[56] References Cited

U.S. PATENT DOCUMENTS

| | | | |
|---|---|---|---|
| 4,378,607 | 4/1983 | Wadsworth | 623/20 |
| 4,467,801 | 8/1984 | Whiteside | 606/88 |
| 4,624,250 | 11/1986 | Saunders et al. | 606/84 |
| 4,686,978 | 8/1987 | Wadsworth | 606/84 |
| 4,718,414 | 1/1988 | Saunders et al. | 606/80 |
| 5,601,565 | 2/1997 | Huebner | 606/89 X |

FOREIGN PATENT DOCUMENTS 2 215 610  9/1989  United Kingdom ............ 623/20

OTHER PUBLICATIONS

Zimmer brochure entitled Coonrad/Morrey Total Elbow, pp. 1–12, Copyright 1989, 1992, 1993.

Biomet brochure entitled Kudo Elbow System, pp. 1–12, Copyright 1989.

Orthopedic Equipment Company, Inc. brochure entitled Stanmore Total Elbow Replacement, 4 pages, Copyright 1978.

Osteonics Corp. brochure regarding Technique for Implantation of the Linked Semi-Constrained Osteonics Total Elbow Prostheses, pp. 1–4, cover page and 4 additional sheets, Copyright 1989.

Chapter 12, entitled Capitellocondylar Total Elbow Arthroplasty, from *Master Techniques in Orthopaedic Surgery, The Elbow*, Raven Press, Ltd., pp. 209–230, Copyright 1994.

*Primary Examiner*—Mary Beth Jones
*Attorney, Agent, or Firm*—Harness, Dickey & Pierce, P.L.C.

[57] ABSTRACT

Instrumentation and method for surgically preparing the natural capitellum of an elbow joint to receive a capitellum prosthesis in elbow arthroplasty, including a reference pin that is first inserted into the natural capitellum along an axis extending through its spherical articulating surface and the approximate center of the partial sphere generally defining the natural capitellum. Cutting instruments, including an end cutting mill, an anterior/posterior cutting guide, and a chamfer jig cooperate with the reference pin to permit resurfacing of the natural capitellum in a manner to create a surface geometry corresponding in shape to the mounting surface of a capitellum prosthesis. The reference pin and cutting instruments are removed, after which the capitellum prosthesis is attached to the natural capitellum by fitting the mounting surface of the capitellum prosthesis to the mounting surface established on the natural capitellum.

12 Claims, 2 Drawing Sheets

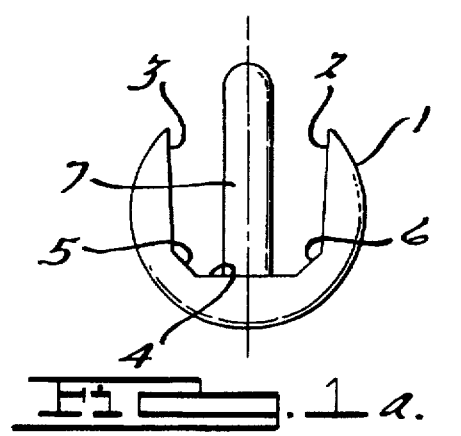
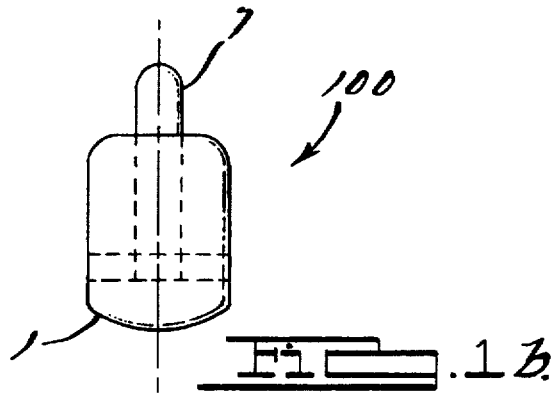
Fig. 1a.  Fig. 1b.
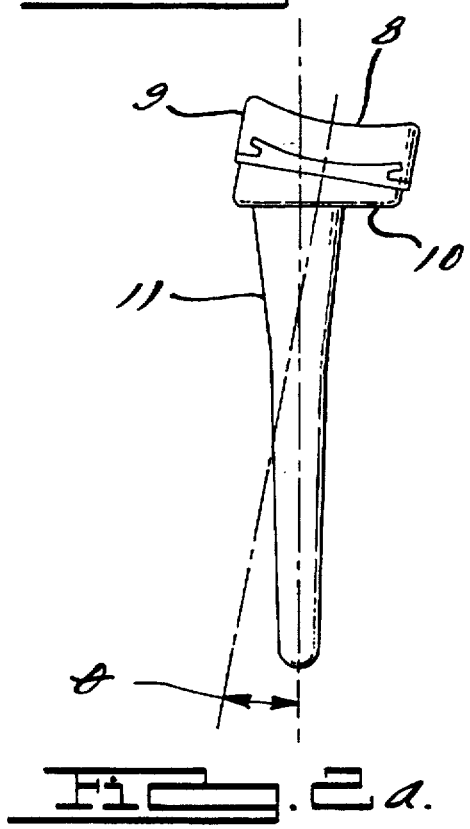
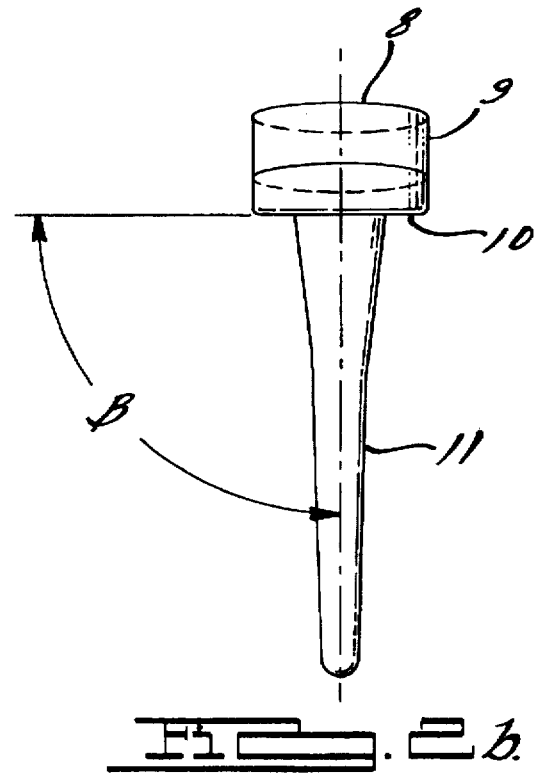
Fig. 2a.  Fig. 2b.
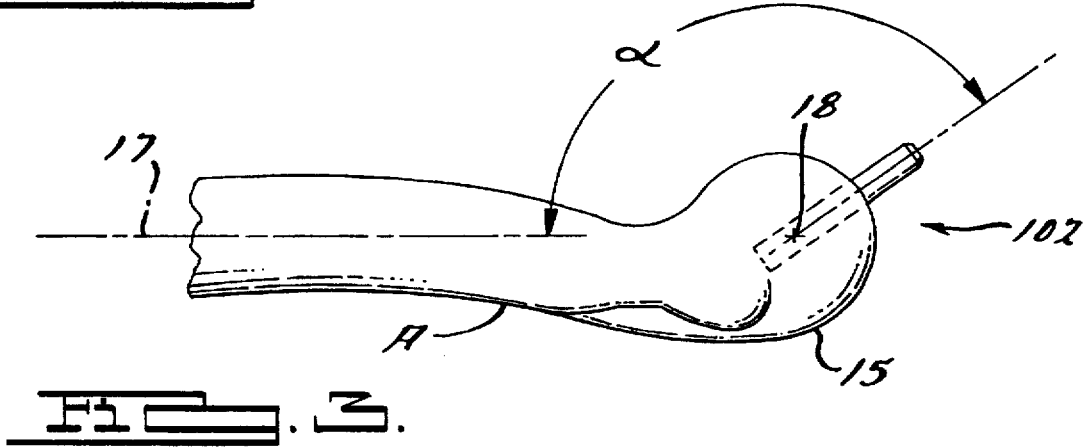
Fig. 3.

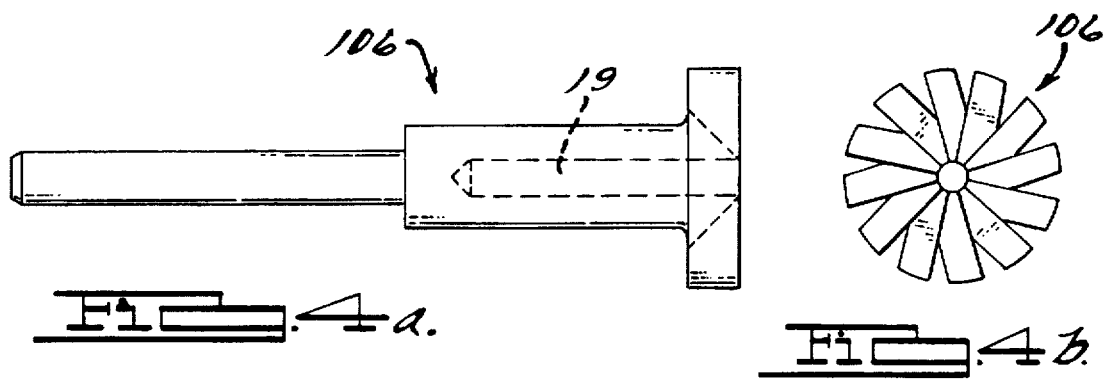
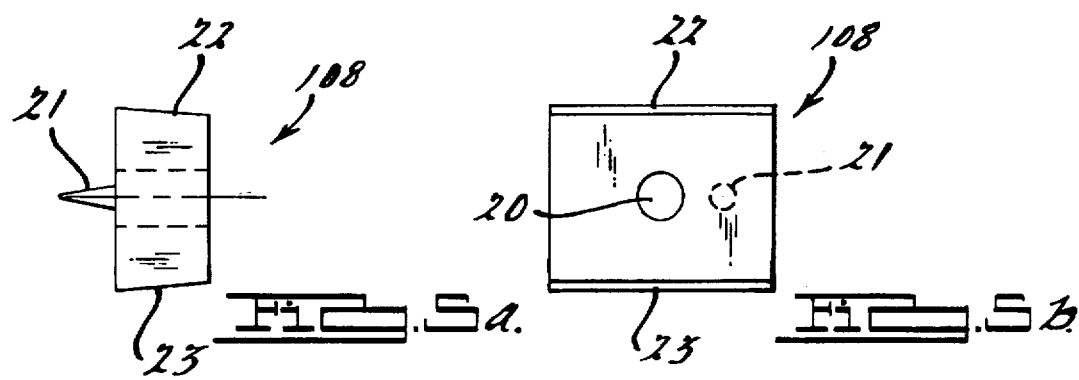
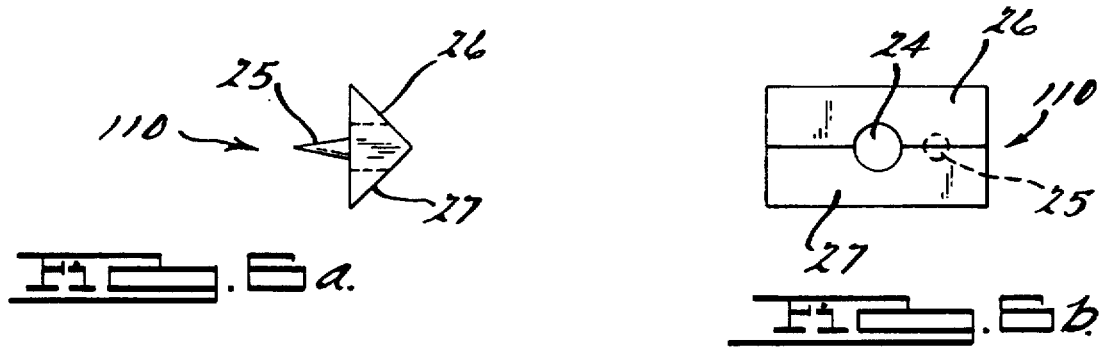
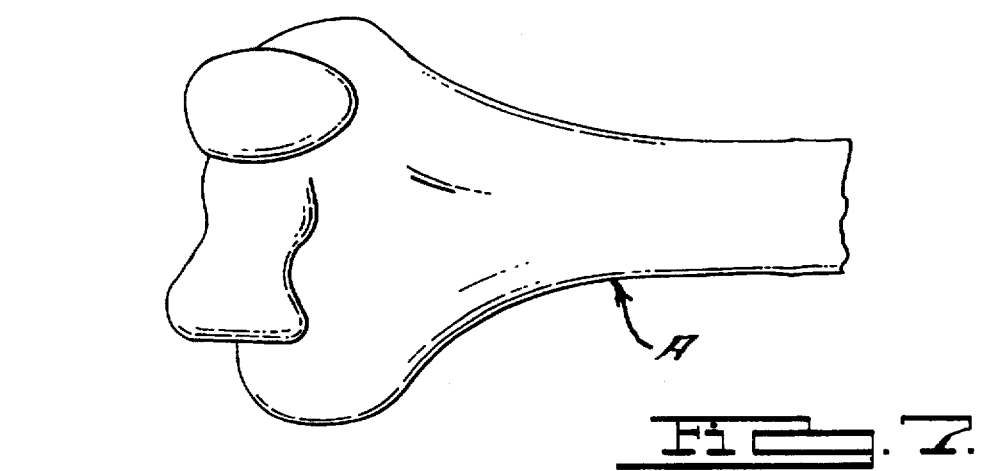

METHOD AND APPARATUS FOR REPLACING THE CAPITELLUM

BACKGROUND OF THE INVENTION

1. Field of the Invention

The present invention relates generally to surgical instrumentation and prosthetic devices used in elbow arthroplasty and, more specifically, to a method and apparatus for resurfacing the capitellum and radius of an elbow.

2. Discussion

Degenerative arthritis, particularly of the radial/humeral articulation elbow joint, has historically seen numerous treatments. For instance, a metallic radial head replacement was commercially available from Codman and Shurtleff, Inc. as early as 1965. One disadvantage of this type of device was that it did not provide a replacement for the humeral side of the articulation and, therefore, long term use of this type of arthroplasty tended to result in erosion of the humeral bone where it articulated with metal.

Excision of the proximal head of the radius, above the annular ligament, has historically been a method of treatment for selectively removing the radial-humeral joint when it has degenerated to the point of causing pain to the patient. This type of excision relieves pain, but can reduce stability of the joint, leading to valgus deformity of the upper limb at the elbow and accelerated degeneration of the remaining ulnar/humeral articulation.

Excision of the proximal head of the radius, along with a prosthetic replacement of the ulnar/humeral articulation, is a common method of treatment of the arthritic elbow. Typically, this prosthetic articulation has been in the form of a linked hinge, or unlinked surface replacement of the ulna and humerus. This is a more severe surgical intervention than is normally chosen when only the radial/humeral articulation is involved.

Complete resurfacing of the radial/humeral, and ulnar/humeral articulations was provided by the ERS® elbow, commercially available from DePuy, Inc., Warsaw, Ind. In this prosthesis, a single metal cap is fitted onto the end of the humerus. This cap is shaped to engage the prosthetically resurfaced ends of both the radius and the ulnar. This is also a more severe surgical intervention than is normally chosen when only the radial/humeral articulation is involved.

A commercial device involving resection of the radial head and replacement with a silastic prosthesis was available at one time from Dow Corning Wright, Inc., Memphis, Tenn. In the articulation of this device, the silastic implant at the proximal end of the radius articulates with the capitellum at the distal end of the humerus. This type of articulation can result in abrasion and deterioration in both the silastic implant and the bone it contacts. Furthermore, silastic material is believed by some to elicit an inflammatory response by the surrounding tissue, especially when it is present in a particulate state.

What is needed then, is a prosthesis of the radial/humeral articulation that replaces the surface of both the radius and humerus bones of the natural elbow. It is also desired to provide a set of instruments for elbow arthroplasty that is minimally invasive, that is easy to use, that permits intra-operative flexibility, and that safely and accurately resects the necessary bone from the proximal radius and the capitellum of the distal humerus.

SUMMARY OF THE INVENTION

The present invention overcomes the problems and disadvantages of the above-described prior art elbow arthroplasty instrumentation and prostheses by providing an improved instrumentation and method for surgically preparing the natural capitellum of the humerus for operatively accepting a capitellum prosthesis.

The invention, in one form thereof, provides a method for preparing the natural spherically-shaped capitellum of the humerus to receive a capitellum prosthesis, by first inserting a reference pin into the natural capitellum along a reference axis extending generally through a point on the articulating surface of the capitellum and the approximate spherical center of the capitellum. At least one cutting instrument is then used in conjunction with the reference pin to shape the capitellum in a manner to provide a mounting geometry that corresponds to a mounting surface on a capitellum prosthesis. The prosthesis is then attached to the capitellum by fitting the mounting surface of the prosthesis to the mounting geometry of the prepared capitellum.

One advantage of the present invention is that by establishing the reference pin along a reference axis that extends generally through the articulating surface and center of the natural capitellum, greater intra-operative flexibility is achieved for cutting the surface of the capitellum and attaching the capitellum prosthesis so as to reestablish natural function of the elbow joint.

Additional advantages and features of the present invention will become apparent from the following description and appended claims, taken in conjunction with the accompanying drawings.

BRIEF DESCRIPTION OF THE DRAWINGS

FIG. 1a is a side elevational view of a capitellum implant of the type to which the present invention pertains;

FIG. 1b is a front elevational view of the capitellum implant of FIG. 1a;

FIG. 2a is a front elevational view of a radial head implant of the type to which the present invention pertains;

FIG. 2b is a side elevational view of the radial head implant of FIG. 2a;

FIG. 3 is a side view of the distal humerus, particularly showing a reference pin inserted along an axis extending generally through the articulating surface and spherical center of the capitellum at an obtuse angle relative the longitudinal axis of the humerus;

FIG. 4a is a side view of an end cutting mill in accordance with a preferred embodiment of the present invention;

FIG. 4b is an end view of the end cutting mill of FIG. 4a;

FIG. 5a is a side view of an anterior/posterior cutting guide in accordance with a preferred embodiment of the present invention;

FIG. 5b is a front view of the anterior/posterior cutting guide of FIG. 5b;

FIG. 6a is a side view of a chamfer jig in accordance with a preferred embodiment of the present invention;

FIG. 6b is a front view of the chamfer jig of FIG. 6a; and

FIG. 7 is a front view of the distal humerus.

DETAILED DESCRIPTION OF THE PREFERRED EMBODIMENT

Referring to FIG. 1, a humeral component 100 of a radial/humeral implant is shown. Humeral component 100 is preferably made of Cobalt-Chrome alloy, but may be made of other biocompatible materials common to the art of orthopedic implant design. The articular surface 1 of the humeral component 100 is preferably spherical in configuration and polished to a mirror finish. Flat surfaces 2 and 3 are located internal to the articular surface 1. The flat surfaces 2 and 3 correspond to anterior and posterior bone resection on the capitellum 102 (shown in FIG. 3), necessary for implantation. The flat surfaces 2 and 3 are configured in opposing positions and provide stable fixation for the implant. A third surface 4 is internal to the articular surface 1. Third surface 4 lies approximately half way between flat surfaces 2 and 3 and is oriented approximately 90 degrees to those surfaces. Surface 4 corresponds to a distal bone resection on the capitellum 102, necessary for implantation. Chamfer surfaces 5 and 6 are flat surfaces that act as chamfers between surfaces 2, 3 and 4. The chamfer surfaces 5 and 6 are shown on a preferred embodiment, but are not essential to the function of the implant. The chamfer surfaces 5 and 6 may be employed to optimize the configuration of the implant and minimize the necessary bone resection. A stem 7 is present on the internal region of the humeral component 100. The stem 7 is not essential to the function of the implant, but may be employed to increase fixation, and to act as a guide during implantation. The internal geometry is generally bead blasted or may be porous coated.

Referring now to FIG. 2, the radial component 104 of the implant is shown. The radial component 104 includes an articular surface 8 made of a high molecular weight polyethylene (UHMWPE) and is otherwise typically made of Cobalt-Chrome alloy. The articular surface 8 of the radial component 104 is generally spherical and concave. The radius of curvature of articular surface 8 is generally greater than or equal to the radius of curvature of surface 1. A side wall 9 comprises the non-articular side wall of the head of the prosthesis and is generally cylindrical in configuration. The bone abutting surface 10 refers to the flat undersurface of the head of the prosthesis. The surface 10 generally corresponds to the proximal bone resection on the radial head, necessary for implantation. The stem 11 of the radial component 104 functions to provide fixation and alignment to the component 104. The stem 11 is oriented normal to surface 10 such that an angle β of approximately 90 degrees is defined therebetween. The cylindrical side walls 9 of the head can be displaced through an angle Θ ranging from approximately 0–20 degrees with respect to the stem 11 without changing the normal 90 degree orientation between stem 11 and surface 10.

An important factor in the successful use of the described radial/humeral prosthesis, is providing the surgeon with instrumentation that is appropriate to the implant and surgical objective. The articulation that is being resurfaced is relatively small, when compared to known elbow arthroplasties that are presently widely used. The necessary incision and retraction can also be relatively small to reduce surgical trauma, but this small opening requires special instrumentation. Additionally, this instrumentation should aid in the proper size and orientation of bone resection, it should allow visualization of the surfaces being resected in preparation for the prosthesis, it should allow variation for intra-operative choices made by the surgeon, it should be simple and easy to use, and it should reduce the likelihood of inadvertent trauma to the neural and vascular structures exposed by the surgical incision.

Prior instrumentation for elbow arthroplasties has relied on free hand use of burrs, osteotomes, or saws. In some cases these cutting tools have been guided by jigs that are aligned with the intramedullary canal of the humerus. Neither of these alternatives is optimally suitable for implantation of the radial/humeral prosthesis described earlier. Free hand use of cutting tools is difficult, inaccurate, and increases the chances for inadvertent trauma in the surgical site. Using jigs that incorporate intramedullary rods necessitates a dramatic increase in the soft tissue exposure, necessitates violating the intramedullary cavity of the humerus, and reduces visibility from the instrumentation linking the I.M. rod with the cutting jigs. The disclosed invention is a set of instruments for implanting the described radial/humeral prosthesis while avoiding the pit falls of previous tools and methods, and achieving the benefits previously described.

An important aspect of the invention is the use of a drill or stud 14, as shown in FIG. 3, that is inserted into the capitellum 15 at an angle α of between approximately 120 degrees and 170 degrees relative to the long axis 17 of the humerus A, and passes through the center 18 of the sphere of the capitellum 15. The orientation of this drill/stud 14 can be determined from intra-operative x-rays, a fluoroscope, visualization of the humerus A, and/or a drill guide that contacts the capitellum through the use of a vee block. Initial position can be done with a smaller diameter drill or pin (not shown) so that ample bone remains for fixation of the drill/stud 14.

An end cutting mill 106, as shown in FIG. 4, has a cylindrical axial cavity 19 (shown in broken lines) that engages the drill/stud 14 after it has been appropriately positioned in the capitellum 15. The cylindrical cavity 19 and drill/stud 14 are appropriately sized such that the end cutting mill 106 is free to rotate and be pressed against the distal end of the capitellum 15, while still maintaining axial orientation between the drill/stud 14 and the end cutting mill 106. In this way small amounts of bone, and then progressively larger amounts of bone, can be milled from the distal humerus A in a predetermined and consistently maintained orientation. This prepares the bone to mate with fixation surface 4 of the prosthesis.

Referring now to FIG. 5, a second guide 108 is then slid over the drill/stud 14 by engaging a cylindrical hole 20 in the guide with the drill/stud 14. The cylindrical hole 20 and drill/stud 14 are appropriately sized such that the second guide 108 is free to rotate and be pressed against the distally resected surface of the capitellum. Axial rotation of the guide 108 is not critical and, therefore, variations in axial rotation judged appropriate by the surgeon can be tolerated since the drill/stud 14 passes through the spherical center 18 of the capitellum 15 and the prosthesis is also spherical. One or more fixation spikes 21 can be present to help stabilize the guide 108.

The guide 108 includes two planer surfaces 22 and 23, that when projected intersect the anterior and posterior aspects of the capitellum 15 in a size and location corresponding to fixation surfaces 2 and 3 of the prosthesis. The planer surfaces 22 and 23 are used as a guide to make the appropriate anterior and posterior resections while still maintaining the same orientation established with the end cutting mill 106 resection. Planer surfaces 22 and 23 can be open planer faces, closed slots for a saw guide, or closed slots for a burr guide. Furthermore, if multiple capitellar prosthesis sizes are provided, corresponding sizes of the second guide 108 will also be provided. As a general practice, a larger size can then be applied, the bone resected, the resection evaluated, and a smaller size is still available for further resection, if necessary.

If the configuration of the capitellar prosthesis accommodates chamfers 5 and 6, a third guide 110 shown in FIG. 6 is provided. The third guide 110 also has a cylindrical hole 24 that is oriented over the drill/stud 14 in the same manner as the second guide 108. The axial rotation of the third guide 110 is matched to the axial rotation of the second guide 108, either visually or through identically oriented fixation spikes 25. In this case, the fixation spikes 25 are adapted to fit into the same holes in the bone that were created by fixation spike 21 from the second guide 108. This properly orients surfaces 26 and 27 to define planer surfaces to resect the capitellum 15 to accommodate fixation surfaces 5 and 6 on capitellar implant 100. This sequence of steps maintains the orientation between the end cutting mill 106 resection, the second guide 108 resection, and the third guide 110 resection. The orientation is determined by the position of the drill/stud 14 and the position of the drill/stud 14 is selected and optimized by the surgeon before any resections are carried out.

An additional benefit derived by this instrumentation is realized on the radial head resection. In this regard, the drill/stud 14 can be inserted down the canal of the radius. The end cutting mill 106 is then advanced against the radial head until the appropriate resection is made. In this way, the drill stud 14 prepares the canal for the stem 11 and the bone resection is made at a normal orientation of 90 degrees between the drill/stud 14 and the resected radial head. This is the same orientation between the stem 11 and the surface 10 that corresponds to the resected radius. The relationships stay constant, even though the angle Θ of the head can vary from the stem.

The foregoing discussion discloses and describes merely an exemplary embodiment of the present invention. One skilled in the art will recognize from such discussion and from the accompanying drawings and claims, that various changes, modifications and variations can be made therein without departing from the spirit and scope of the invention.

What is claimed is:

1. In elbow joint arthroplasty, a method of surgically preparing the natural capitellum of the humerus for accepting a capitellum prosthesis having a stem, wherein the natural capitellum is defined by a partial sphere having a spherical center and a spherical articulating surface, the method comprising the steps of:

determining the spherical center of the natural capitellum;

inserting a reference pin into the natural capitellum through the spherical articulating surface to establish a reference axis;

providing at least one cutting tool adapted to receive the reference pin;

mounting the at least one cutting tool on the reference pin;

shaping the natural capitellum with the at least one cutting tool; and attaching the capitellum prosthesis to the natural capitellum;

wherein the step of inserting the reference pin into the natural capitellum includes the step of orienting the reference axis to extend through a point on the spherical articulating surface and the spherical center of the natural capitellum.

2. The method of claim 1, wherein the step of shaping the natural capitellum includes the step of rotating a portion of the at least one cutting tool about the reference axis.

3. The method of claim 1, wherein the step of shaping the natural capitellum includes the step of forming a first surface on the natural capitellum with the at least one cutting tool, the first surface being generally perpendicular to the reference axis.

4. The method of claim 1, wherein the step of shaping the natural capitellum includes the steps of providing plurality of cutting guides and sequentially mounting each of the plurality of cutting guides on the reference pin.

5. The method of claim 4, wherein the step of providing a plurality of cutting guides includes the step of providing a first cutting guide having first and second spaced apart planer sides, orienting the first and second sides to intersect the anterior and posterior aspects of the natural capitellum, respectively.

6. The method of claim 1, wherein the step of inserting the reference pin into the natural capitellum includes the step of forming an aperture in the natural capitellum, and further wherein the step of attaching the capitellum prosthesis to the natural capitellum includes the step of inserting the stem of the capitellum prosthesis into the aperture.

7. The method of claim 1, wherein the step of inserting the reference pin into the natural capitellum includes the step of forming an aperture in the spherical articulating surface of the natural capitellum, and further wherein the step of attaching the capitellum prosthesis to the natural capitellum includes the step of inserting the stem of the capitellum prosthesis into the aperture.

8. In elbow joint arthroplasty, a method of surgically preparing the natural capitellum of the humerus for accepting a capitellum prosthesis having a stem, wherein the natural capitellum is defined by a partial sphere having a spherical center and a spherical articulating surface, the method comprising the steps of:

determining the spherical center of the natural capitellum;

inserting a reference pin into the natural capitellum through the spherical articulating surface to establish a reference axis;

forming a first surface on the natural capitellum adapted to correspond substantially in shape with a portion of the capitellum prosthesis, the first surface being generally perpendicular to the reference axis; and attaching the capitellum prosthesis to the natural capitellum so as to abut the first surface on the natural capitellum with the portion of the capitellum prosthesis.

9. The method of claim 8, wherein the step of forming a first surface on the natural capitellum comprises the steps of:

providing at least one cutting tool adapted to receive the reference pin;

mounting the at least one cutting tool on the reference pin; and shaping the natural capitellum with the at least one cutting tool.

10. The method of claim 9, wherein the step of shaping the natural capitellum includes the step of rotating a portion of the at least one cutting tool about the reference axis .

11. The method of claim 9, wherein the step of shaping the natural capitellum includes the steps of providing a plurality of cutting guides and sequentially mounting each of the plurality of cutting guides on the reference pin.

12. The method of claim 11, wherein the step of providing a plurality of cutting guides includes the step of providing a first cutting guide having first and second spaced apart planer sides, orienting the first and second sides to intersect the anterior and posterior aspects of the natural capitellum, respectively.

* * * * *